(12) United States Patent
Diekmeyer et al.

(10) Patent No.: US 8,336,576 B2
(45) Date of Patent: Dec. 25, 2012

(54) COMPRESSED AIR SUPPLY DEVICE FOR MOTOR VEHICLES

(75) Inventors: Heinrich Diekmeyer, Barsinghausen (DE); Horst Heinrich, Hannover (DE); Bernd Strilka, Hannover (DE)

(73) Assignee: WABCO GmbH, Hannover (DE)

( * ) Notice: Subject to any disclaimer, the term of this patent is extended or adjusted under 35 U.S.C. 154(b) by 740 days.

(21) Appl. No.: 12/309,163

(22) PCT Filed: Jun. 12, 2007

(86) PCT No.: PCT/EP2007/005146
§ 371 (c)(1),
(2), (4) Date: Jan. 9, 2009

(87) PCT Pub. No.: WO2008/014843
PCT Pub. Date: Feb. 7, 2008

(65) Prior Publication Data
US 2010/0059126 A1    Mar. 11, 2010

(30) Foreign Application Priority Data
Aug. 1, 2006  (DE) .......................... 10 2006 035 772

(51) Int. Cl.
*E03B 5/00* (2006.01)
*F04B 49/00* (2006.01)
(52) U.S. Cl. ............... 137/565.11; 73/29.01; 73/863.41; 73/863.61
(58) Field of Classification Search ............. 137/565.11, 137/565.18, 565.35; 73/863.61, 29.01, 863.58, 73/863.81, 863.41, 863.71
See application file for complete search history.

(56) References Cited

U.S. PATENT DOCUMENTS

| | | | | |
|---|---|---|---|---|
| 3,443,434 A | * | 5/1969 | Baker et al. | .................. 73/202.5 |
| 4,131,011 A | | 12/1978 | Ling | |
| 5,460,054 A | * | 10/1995 | Tran | ........................... 73/863.61 |
| 5,730,942 A | | 3/1998 | Megerle et al. | |
| 5,738,338 A | * | 4/1998 | Sutehall | ..................... 254/134.4 |
| 5,834,657 A | * | 11/1998 | Clawson et al. | ........... 73/863.61 |

FOREIGN PATENT DOCUMENTS

| | | | |
|---|---|---|---|
| DE | 35 04 884 A1 | | 7/1986 |
| DE | 3504884 A | * | 7/1986 |
| DE | 37 24 149 A1 | | 11/1988 |
| DE | 10 2004 026624 B3 | | 6/2005 |
| EP | 0 191 151 A | | 8/1986 |
| EP | 0 717 282 A | | 6/1996 |
| JP | 2003 193830 A | | 7/2003 |

* cited by examiner

*Primary Examiner* — Len Tran
*Assistant Examiner* — Jennifer Gordon
(74) *Attorney, Agent, or Firm* — Kramer Levin Naftalis & Frankel LLP

(57) ABSTRACT

A compressed air supply system for motor vehicles includes a compressor, control electronics, an air dryer having an inlet channel for non-dried compressed air, an outlet channel for the dried compressed air, and a dehumidification device through which the compressed air to be dried can flow, a pressure regulator having an outlet valve for controlling the compressor between an idle phase and a load phase, a multi-circuit safety valve that is connected to the outlet channel of the air dryer via a compressed air line, and over-flow valves for the individual circuits, a regeneration valve and a moisture sensor for detecting the atmospheric moisture in the compressed air flowing in the compressed air line. To reduce the detrimental effects of admixtures and components of the compressed air on the moisture sensor, the moisture sensor is located in a bypass channel of the compressed air line.

11 Claims, 2 Drawing Sheets

COMPRESSED AIR SUPPLY DEVICE FOR MOTOR VEHICLES

FIELD OF THE INVENTION

The present invention generally relates to a compressed air supply device for motor vehicles.

BACKGROUND OF THE INVENTION

In compressed air supply devices of motor vehicles, it is known how to measure the relative humidity at the outlet of the air dryer or in a compressed air tank by means of a moisture sensor designed as a moisture switch, the output signals of which are supplied to evaluation/control electronics. In the event that the relative humidity exceeds a threshold value, the evaluation/control electronics initiate regeneration of the dehumidification device or generate a warning signal to indicate, for example, that the dehumidification device has greatly deteriorated in terms of efficiency and/or that it must be replaced. As an improvement of the moisture switch, capacitive moisture sensors, in which a hygroscopic polymer layer, for example, is disposed as a dielectric between two capacitor electrodes, are, among other options, also used. Depending on the ambient water vapor pressure, more or less water is absorbed in the polymer layer. Thereby, the dielectric constant and, in turn, the capacitance of the capacitor changes. As is known, the compressed air in commercial vehicles is contaminated with different constituents of the intake air, some harmful for the polymer layer, and with harmful oil and oil-decomposition products from the compression process in the compressor. As a result, the effectiveness of the capacitive principle is greatly impaired by such contaminants after a prolonged exposure time, thus, in particular, reducing the accuracy and shortening the useful life of the moisture sensor.

SUMMARY OF THE INVENTION

Generally speaking, in accordance with embodiments of the present invention, a compressed air supply device for motor vehicles is provided that overcomes deficiencies of conventional devices. The compressed air supply device for motor vehicles in accordance with embodiments of the present invention includes a compressor, control electronics, an air dryer that has an inlet duct for undried compressed air, an outlet duct for dried compressed air and a dehumidification device through which the compressed air to be dried can flow, a pressure regulator with outlet valve for control of the compressor between an idling phase and a load phase, a multi-circuit safety valve that is in communication with the outlet duct of the air dryer via a compressed air line and that has overflow valves for the individual circuits, a regeneration valve and a moisture sensor for sensing relative humidity mounted in a bypass duct of the compressed air line.

In measuring systems, it is normal practice to come into contact as closely as possible with the measured variable. In contrast, the present invention proposes to maintain a distance systematically from the actual measured medium, in order to compensate for the restricted tolerance of the hygroscopic polymer for media and to conduct the measurement of relative humidity in the bypass duct of the compressed air line. For this purpose, the bypass duct has correspondingly smaller cross section and volume flow than the actual compressed air line.

A parallel flow of dried compressed air passes through the bypass duct, the fraction of compressed air flowing through the bypass duct having the same condition in terms of moisture content as the main fraction of dehumidified compressed air flowing directly to the outlet port. At the same time, however, the amount of contaminants impinging on the moisture sensor is correspondingly smaller, whereby, the harmful effects on the moisture-sensitive polymer layer are greatly reduced. Because of the reduction of the effect of contaminating, or, in other words, harmful active substances on the capacitance-determining polymer layer, the calibrated accuracy of the moisture sensor is preserved over a longer time period and, thereby, the useful life of the moisture sensor is prolonged on the whole. The inventive design therefore optimizes the monitoring of the air dryer function for diagnostic and control purposes, for example, for regeneration and systematic replacement of the dehumidification device (desiccant cartridge).

The measurement of the relative humidity of the dried compressed air in the bypass duct can be accomplished not only directly downstream from the air dryer outlet and upstream from the multi-circuit protective valve but also in a working circuit of the multi-circuit safety valve.

In one embodiment of the present invention, the response time of the moisture sensor is improved by constructing the bypass duct such that turbulent flow is developed in the bypass duct.

Preferably the moisture sensor is installed vertically above the compressed air duct, whereby, an improvement of the vibration resistance is achieved for moisture sensor elements having unattached wire ends.

Another embodiment of the present invention provides for placing the moisture sensor holder in communication with the compressed air line via a duct, in order to give excess (condensed) moisture and also contaminants the opportunity to drain into the compressed air duct.

Accordingly, it is an object of the present invention to provide a compressed air supply device of the general type under consideration that reduces the harmful effects of contaminants on the polymer layer forming the dielectric of the moisture sensor and to prevent the influence on the humidity measurement as regards accuracy and useful life due to harmful impurities and constituents of the compressed air.

Still other objects and advantages of the present invention will in part be obvious and will in part be apparent from the specification.

The present invention accordingly comprises the features of construction, combination of elements, and arrangements of parts which will be exemplified in the constructions hereinafter set forth, and the scope of the invention will be indicated in the claims.

BRIEF DESCRIPTION OF THE DRAWINGS

The present invention will be discussed in greater detail hereinafter on the basis of the attached drawings, wherein.

DETAILED DESCRIPTION OF THE PREFERRED EMBODIMENTS

Figure 1:
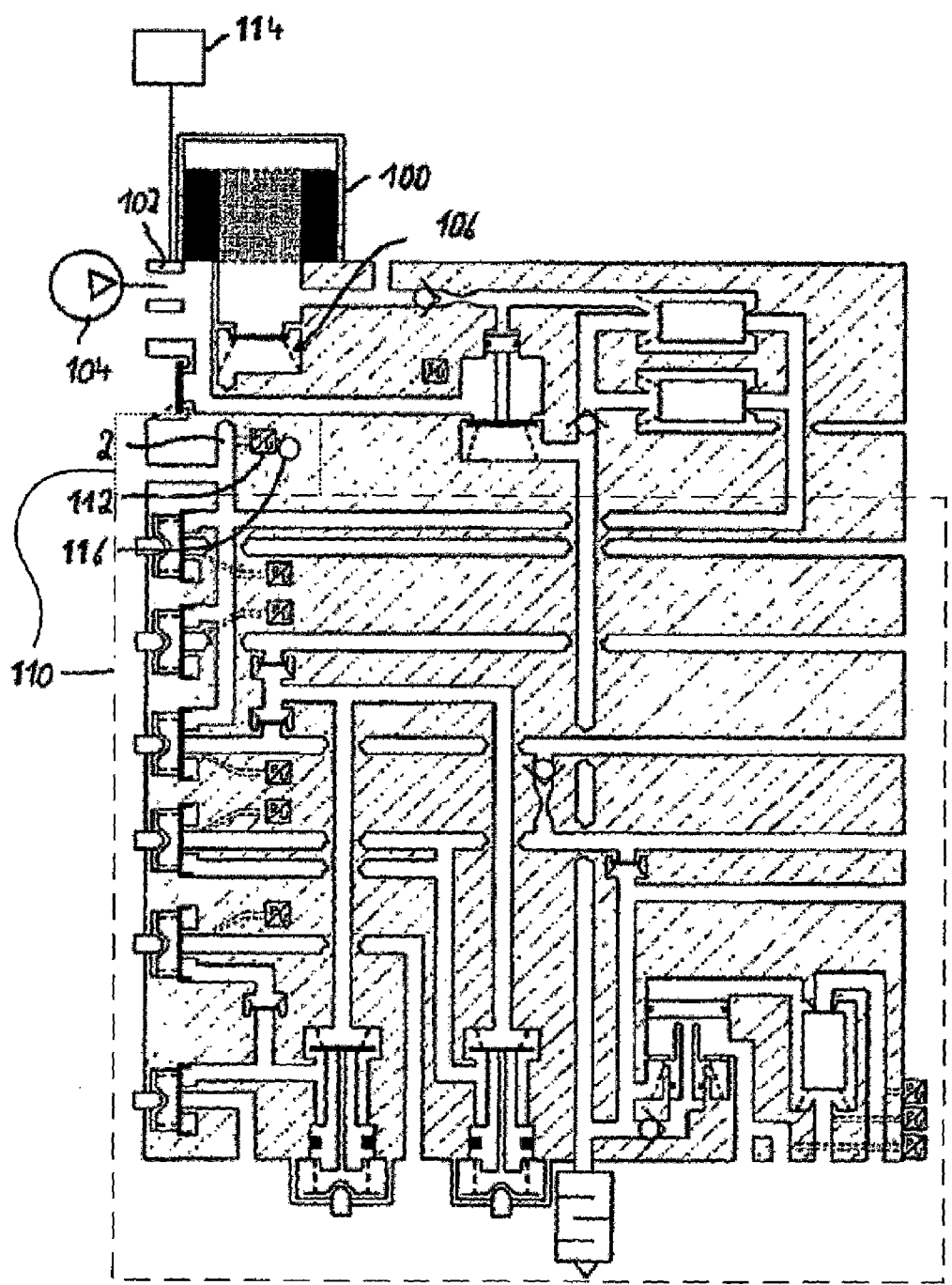
FIG. 1 shows a conventional compressed air supply device with a moisture sensor.

Referring now to the drawing figures, FIG. 1 shows a compressed air supply device for motor vehicles, with control electronics 114, and a compressed air dryer 100, to which compressed air from a compressor 104 is fed via a port 102.

The compressed air flows through compressed air dryer 100 and then flows further via a check value 106 and a compressed air line 2 to a multi-circuit safety value 110. FIG. 1 shows two exemplary variants of multi-circuit safety valve 110 (e.g., a first in which a moisture sensor 112 is at an inlet of multi-circuit safety valve 110, and a second in which the moisture sensor 112 is at an outlet of multi-circuit safety valve 110). Multi-circuit safety valve 110 is not the subject focus of the present application and, therefore, is not discussed in greater detail hereafter.

In one embodiment, moisture sensor 112 is disposed in pressure line 2 leading to the multi-circuit safety valve.

Figure 2:
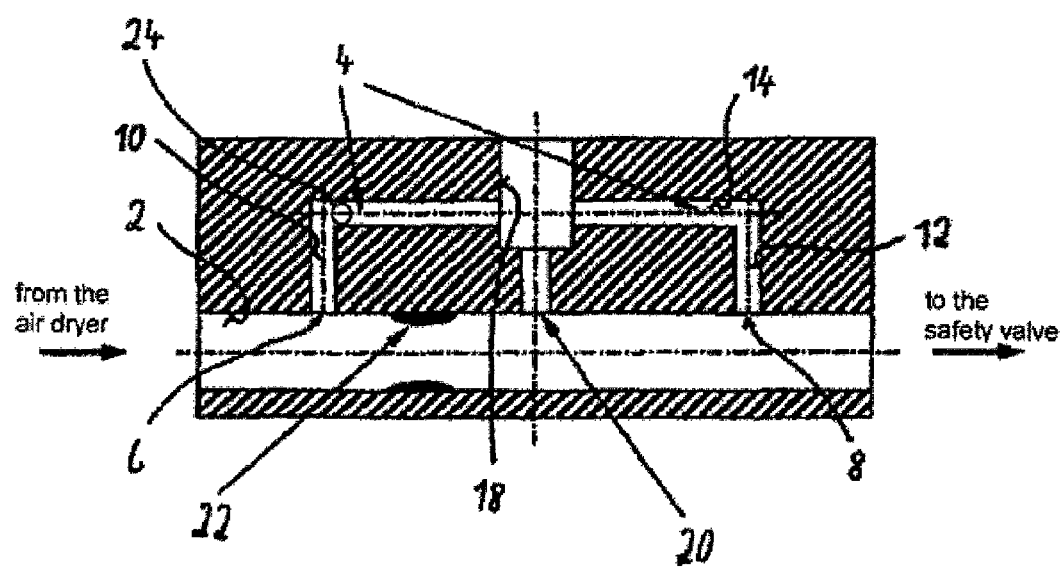
FIG. 2 is a schematic diagram of a device for moisture measurement in accordance with an embodiment of the present invention.

According to embodiments of the present invention, the moisture measurement by means of moisture sensor 112 takes place not directly in compressed air line 2 on the outlet side of compressed air dryer 100 but, rather, in a bypass duct 4 of pressure line 2, as is illustrated in more detail in FIG. 2. Thus, bypass duct 4 is provided between the outlet of compressed air dryer 100 and multi-circuit safety valve 110.

Bypass duct 4 is provided with a bypass inlet 6 and a bypass outlet 8. As illustrated, bypass duct 4 is preferably U-shaped and has a bypass inlet duct 10 branched vertically from pressure line 2, a bypass outlet duct 12 opening vertically into pressure line 2 and a connecting duct 14 running parallel to pressure line 2 and placing bypass inlet duct 10 in communication with bypass outlet duct 12. Connecting duct 14 is in communication with a holder, formed by a recess 18, for a moisture sensor (not illustrated). Recess 18 extends substantially vertically downward beyond connecting duct 14 and, via a drain duct 20 functioning as a condensate drain, is in communication with pressure line 2. Via this drain duct, contaminants such as oil fractions are again discharged into pressure line 2.

Bypass duct 4 and holder 18 for the moisture sensor can be constructed in the air dryer, in the multi-circuit safety valve or in a separate component that can be inserted into pressure line 2. Holder 18 is preferably accessible from the outside.

Heating element 116 for regenerating and readjusting the moisture sensor can be disposed in moisture sensor holder 18 in addition to or in combination with the moisture sensor.

Advantageously, a line constriction 22 (orifice) for generating a dynamic pressure can be formed in compressed air line 2 between bypass inlet 6 and bypass outlet 8, whereby, a forced flow of compressed air into bypass duct 4 can be achieved.

Filtering device 24, for filtering out contaminants, can be disposed in the part of bypass duct 4 leading to the moisture sensor, whereby, a further reduction of the penetration of harmful substances to the moisture sensor can be achieved.

Bypass duct 4 is preferably constructed and arranged such that the partial stream of compressed air flowing in bypass duct 4 passes as a turbulent flow through the bypass duct, whereby, an improvement of the response time of the moisture sensor can be achieved.

The moisture sensor is preferably installed vertically, whereby, an improvement of vibration resistance can be achieved for moisture sensor elements with unattached wire ends.

It will thus be seen that the objects set forth above, among those made apparent from the preceding description, are efficiently attained, and since certain changes may be made in the above constructions without departing from the spirit and scope of the invention, it is intended that all matter contained in the above description or shown in the accompanying drawings shall be interpreted as illustrative and not in a limiting sense.

It is also to be understood that the following claims are intended to cover all of the generic and specific features of the invention herein described and all statements of the scope of the invention which, as a matter of language, might be said to fall therebetween.

What is claimed is:

1. A compressed air supply device for motor vehicles, comprising: a compressor that is switchable between an idling phase and a load phase; control electronics; an air dryer, said air dryer including an inlet duct for undried compressed air, and an outlet duct for dried compressed air; a multi-circuit safety valve in communication with said outlet duct of said air dryer via a compressed air line; and a moisture sensor mounted in a bypass duct of said compressed air line for sensing relative humidity of compressed air flowing in said compressed air line, said bypass duct being in communication with said compressed air line via a condensate drain line that provides a communication path between said bypass duct and said compressed air line, said communication path being separate from an inlet duct and an outlet duct of said bypass duct; further comprising a holder for said moisture sensor in said compressed air line, said holder in communication with said bypass duct; wherein said holder is directly coupled to said condensate drain line.

2. A compressed air supply device according to claim 1, wherein said bypass duct is located above said compressed air line.

3. A compressed air supply device according to claim 1, wherein said holder for said moisture sensor is in communication with said compressed air line via said condensate drain line.

4. A compressed air supply device according to claim 1, wherein said holder for said moisture sensor includes a heating element for regeneration of said moisture sensor.

5. A compressed air supply device according to claim 1, wherein said compressed air line includes a line constriction between said inlet duct of said bypass duct and said outlet duct of said bypass duct for generation of a dynamic pressure.

6. A compressed air supply device according to claim 1, further comprising a filtering device for filtering contaminants, said filtering device being located in a part of said bypass duct leading to said moisture sensor.

7. A compressed air supply device according to claim 1, wherein said bypass duct is configured to permit a partial stream of compressed air flowing in said bypass duct to pass as a turbulent flow through said holder for said moisture sensor and to impinge turbulently on said moisture sensor.

8. A compressed air supply device according to claim 1, wherein said holder for said moisture sensor holds said moisture sensor in a vertical position.

9. A compressed air supply device according to claim 1, wherein said holder for said moisture sensor is formed by a recess that extends through and beyond said bypass duct.

10. A compressed air supply device according to claim 1, wherein said holder for said moisture sensor is accessible from the outside.

11. A compressed air supply device according to claim 1, wherein said bypass duct and said holder for said moisture sensor are located in one of (i) said air dryer, (ii) said outlet duct of said air dryer upstream from said multi-circuit safety valve, (iii) a working circuit of said multi-circuit safety valve and (iv) a separate component inserted into said compressed air line.

* * * * *